(12) United States Patent
Brue et al.

(10) Patent No.: US 12,070,338 B2
(45) Date of Patent: Aug. 27, 2024

(54) PREDICTING SUSCEPTIBILITY OF LIVING ORGANISMS TO MEDICAL CONDITIONS USING MACHINE LEARNING MODELS

(71) Applicant: General Genomics, Inc., Oklahoma City, OK (US)

(72) Inventors: Daniel Alan Brue, Edmond, OK (US); Warren Dennis Gieck, Calgary (CA); Aronjol David Rosenthal, Midland, TX (US)

(73) Assignee: GENERAL GENOMICS, INC., Oklahoma City, OK (US)

( * ) Notice: Subject to any disclaimer, the term of this patent is extended or adjusted under 35 U.S.C. 154(b) by 830 days.

(21) Appl. No.: 17/207,434

(22) Filed: Mar. 19, 2021

(65) Prior Publication Data

US 2021/0307700 A1    Oct. 7, 2021

Related U.S. Application Data

(60) Provisional application No. 63/005,912, filed on Apr. 6, 2020.

(51) Int. Cl.
| | |
|---|---|
| A61B 5/00 | (2006.01) |
| G06N 20/00 | (2019.01) |
| G16H 10/20 | (2018.01) |
| G16H 10/60 | (2018.01) |
| G16H 50/20 | (2018.01) |

(Continued)

(52) U.S. Cl.
CPC .......... *A61B 5/7275* (2013.01); *A61B 5/7267* (2013.01); *G06N 20/00* (2019.01); *G16H 10/20* (2018.01); *G16H 10/60* (2018.01); *G16H 50/20* (2018.01); *G16H 50/70* (2018.01); *A61B 5/0022* (2013.01); *A61B 5/0205* (2013.01); *A61B 5/021* (2013.01); *A61B 5/091* (2013.01); *A61B 5/14542* (2013.01); *A61B 5/14546* (2013.01); *A61B 5/4806* (2013.01); *A61B 5/4869* (2013.01); *A61B 2560/0242* (2013.01)

(58) Field of Classification Search
None
See application file for complete search history.

(56) References Cited

U.S. PATENT DOCUMENTS

| | | | |
|---|---|---|---|
| 2008/0201280 A1 | 8/2008 | Martin et al. | |
| 2009/0069787 A1* | 3/2009 | Estes | G16H 40/67 |
| | | | 604/151 |

(Continued)

OTHER PUBLICATIONS

International Search Report and Written Opinion received for PCT Patent Application No. PCT/US2021/024187, mailed on Jul. 15, 2021, 10 pages.

(Continued)

*Primary Examiner* — Alan Chen
(74) *Attorney, Agent, or Firm* — ArentFox Schiff LLP (57) ABSTRACT

Embodiments of the present disclosure generally relate to methods for analyzing outcomes of illnesses, such as COVID-19, on living organisms. More particularly, embodiments of the present disclosure relate to methods for identifying risk of illness based on genetic markers and other available data, predicting results of mass exposure to an Illness based on a populations genomes and other available data, and providing indicators and methods of visualization for probability of illness in any living organism.

10 Claims, 6 Drawing Sheets

(51) Int. Cl.
*G16H 50/70* (2018.01)
*A61B 5/0205* (2006.01)
*A61B 5/021* (2006.01)
*A61B 5/091* (2006.01)
*A61B 5/145* (2006.01)

(56) References Cited

U.S. PATENT DOCUMENTS

| | | | |
|---|---|---|---|
| 2019/0096526 A1 | 3/2019 | Hirsch et al. | |
| 2019/0180882 A1* | 6/2019 | Han | G16H 50/30 |
| 2019/0311301 A1* | 10/2019 | Pyati | G06F 16/901 |
| 2020/0005901 A1 | 1/2020 | Cohen et al. | |
| 2020/0303072 A1 | 9/2020 | Drokin et al. | |
| 2020/0365229 A1 | 11/2020 | Fields et al. | |
| 2021/0174168 A1* | 6/2021 | Dalli | G06N 3/045 |
| 2021/0304408 A1* | 9/2021 | Chaganti | G06T 7/11 |
| 2021/0307701 A1 | 10/2021 | Brue et al. | |

OTHER PUBLICATIONS

Yassar, "Featurization," Nov. 4, 2019, 7 pages.
Randle et al., "Midlander creates algorithm to predict likelihood of infection," MRT.com/Midland Reporter Telegram, Apr. 16, 2020, 14 pages.
Accesswire, "Press Release: ZoomAway Jointly Develops Patent Pending App to Provide Business Safety Rating and Certification During COVID-19," May 19, 2020, 17 pages.
Curo46, "Invest in General Genomics Inc.," 2020, 15 pages.
Curo46, "Our Story: Where It All Began," 2020, 4 pages.

\* cited by examiner

PREDICTING SUSCEPTIBILITY OF LIVING ORGANISMS TO MEDICAL CONDITIONS USING MACHINE LEARNING MODELS

CROSS-REFERENCE TO RELATED APPLICATIONS

This application claims benefit to U.S. Provisional Patent Application Ser. No. 63/005,912, entitled "Susceptibility To Illnesses (Viruses, Bacterial Infections, Cancers) Based On Genetic Markers", filed Apr. 6, 2020, and assigned to the assignee hereof, the contents of which are hereby incorporated by reference in its entirety.

BACKGROUND

Field

Embodiments of the present disclosure generally relate to methods for analyzing outcomes of illnesses, such as COVID-19, on living organisms.

Description of the Related Art

Conventional methods for analyzing the outcomes of illnesses on living organisms are generally qualitative and not quantitative.

Therefore, there is a need in the art for more accurate analysis of the outcomes of illnesses on living organisms.

SUMMARY

Embodiments of the present disclosure generally relate to methods for analyzing outcomes of illnesses, such as COVID-19, on living organisms. More particularly, embodiments of the present disclosure relate to methods for identifying risk of illness based on genetic markers and other available data.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope. The disclosure may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Embodiments of the present disclosure generally relate to methods for analyzing outcomes of illnesses, such as COVID-19, on living organisms. More particularly, embodiments of the present disclosure relate to methods for identifying risk of illness based on genetic markers and other available data, predicting results of mass exposure to an Illness based on a populations genomes and other available data, and providing indicators and methods of visualization for probability of illness in any living organism.

Definitions

As used herein, "living organism" refers to any human, animal, plant or other organism that is living or was considered alive at any point.

As used herein, "illness" refers to viruses, bacterial infections, and cancers.

Description

Figure 1:
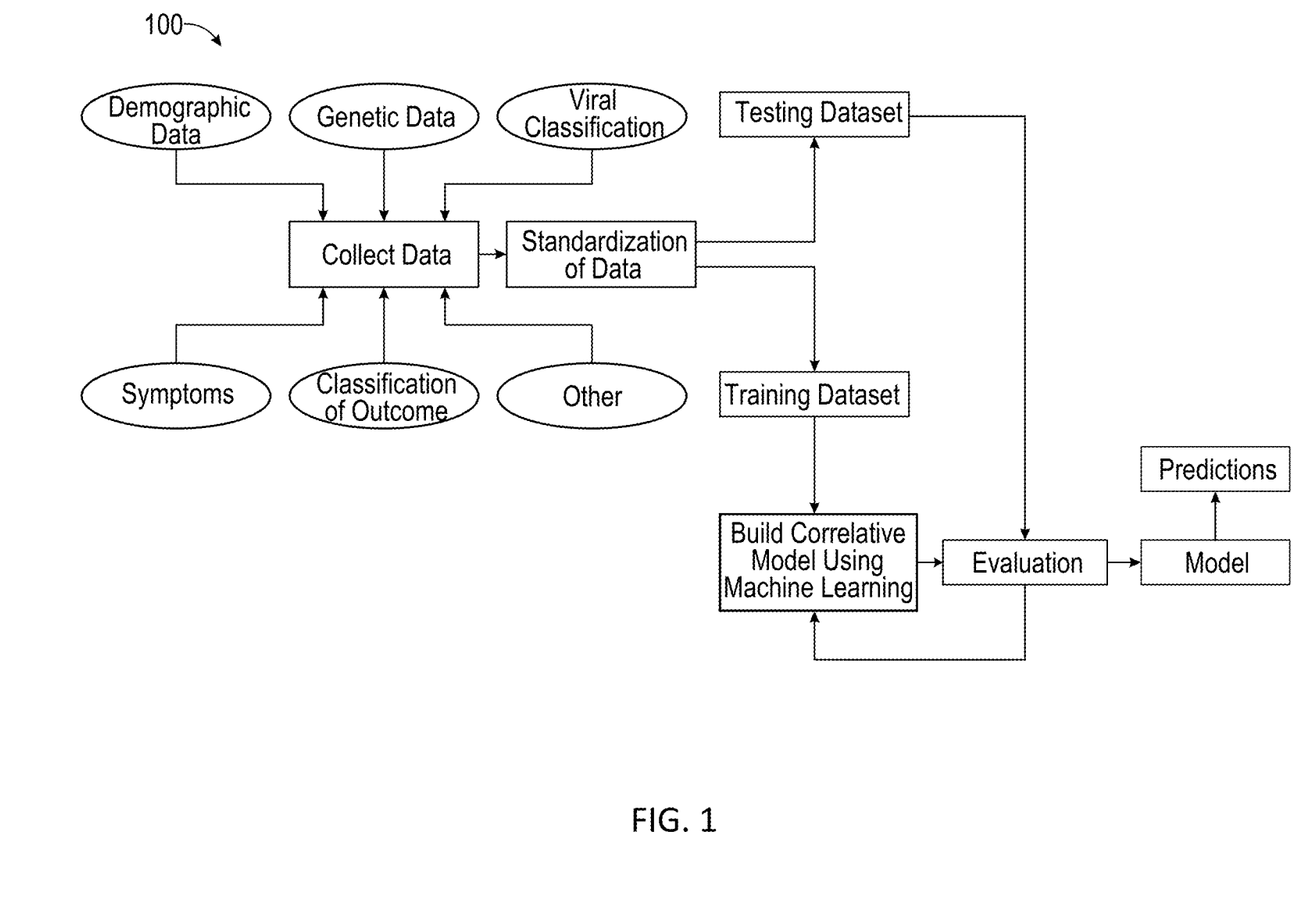
FIGS. 1-3 illustrate flow charts of a method according to embodiments of the present disclosure.
Figure 2:
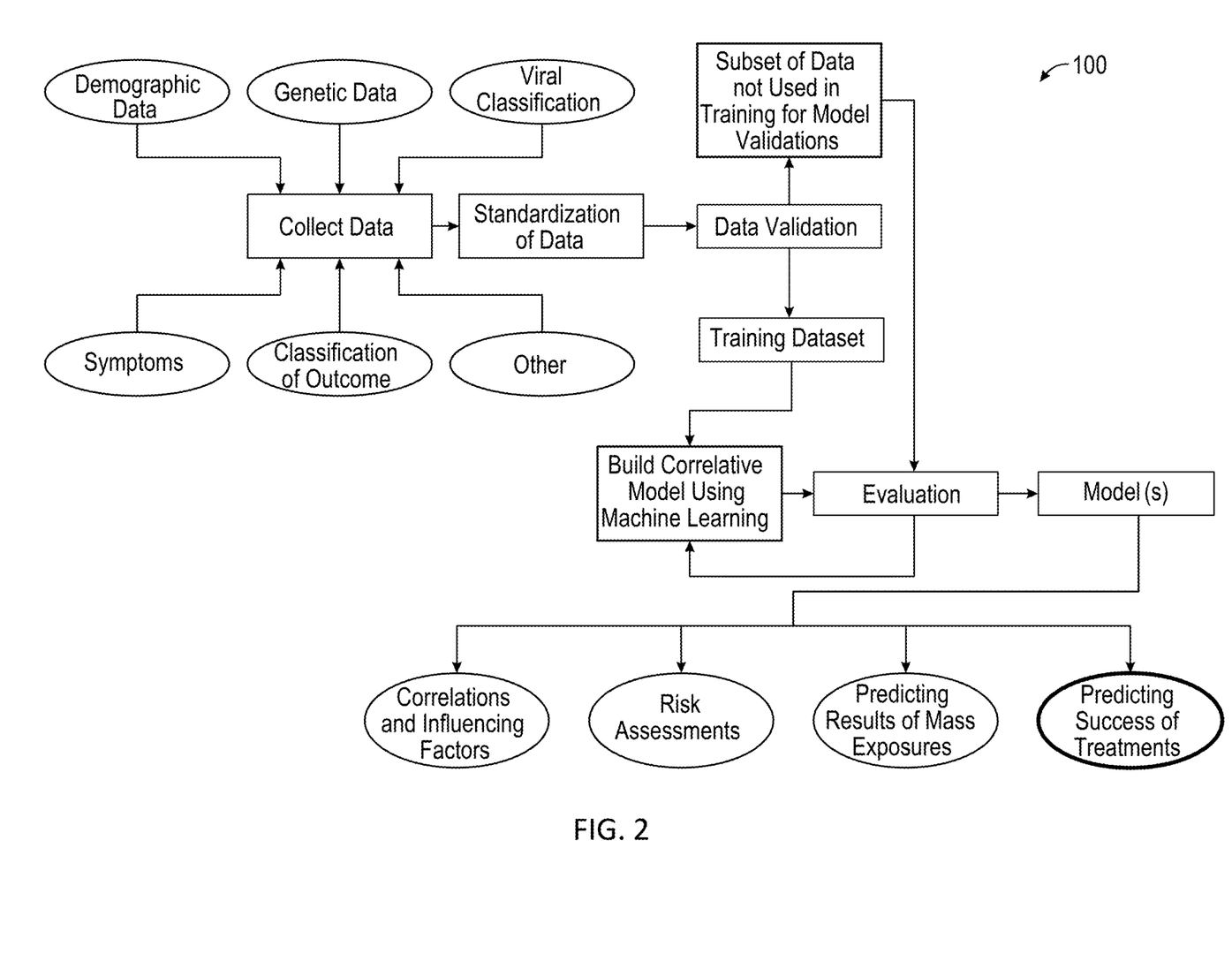
Figure 3:
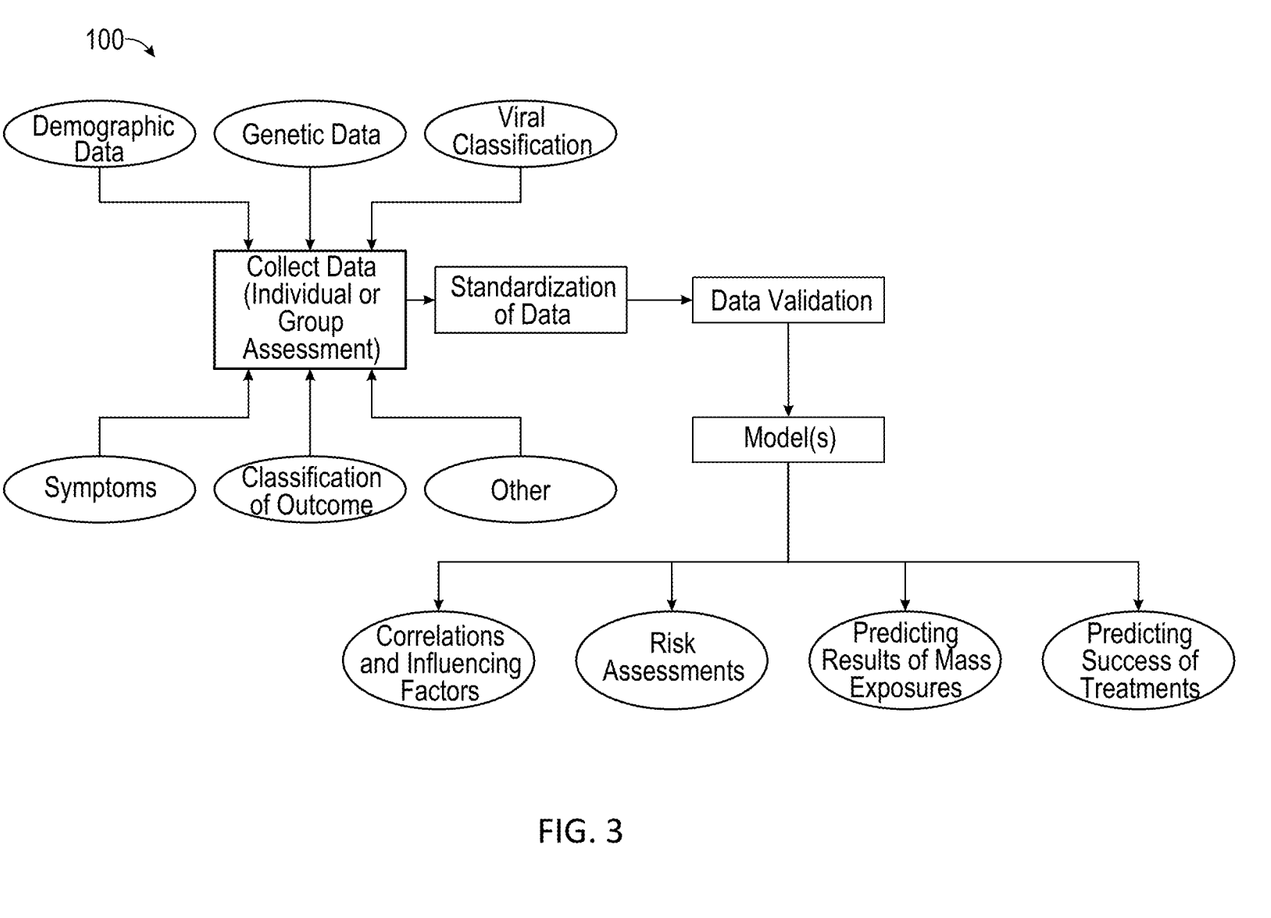

FIG. 1 illustrates a flow chart of a method 100 according to embodiments of the present disclosure. The method 100 generally includes collecting data, standardizing the collected data, generating a testing data set and a training data set, building a correlative model using machine learning, and providing predictions regarding outcomes of illness on living organisms using the correlative model. As shown in FIG. 2, the testing data set is a subset of data used to validate the model. As shown in FIG. 1, the method 100 includes generating quantitative predictions, examples of which shown in FIGS. 2 and 3.

The minimum data required includes (1) classification of outcome(s) from an illness, such as carrier, non-symptomatic, mild/non-critical (no hospitalization), non-critical (hospitalization), critical or intensive care (hospitalization), death, or other, and/or (2) symptom details from an illness.

Other data includes, but is not limited to, all past, current, and future medical test results, DNA analysis, virus type/taxonomic classification, demographics (age, ethnicity, eye color, skin color, hair color, etc.), climate/location (location (ZIP/postal code)), date (current average weather, seasonality), environmental data (prescriptions, lung capacity, smoker, alcohol consumption, etc.), prior medical procedures and conditions (cancer, high blood pressure, diabetes, pneumonia, bronchitis, hay fever/asthma, viral infections/other diseases (COVID, mumps, measles, chick pox, malaria, lupus or other autoimmune disease), vaccinations (MMR, flu shot, etc.)), blood tests (antibodies, blood type, plasma, O2 volume, lactic dehydrogenase (LDH), lymphocyte, high-sensitivity C-reactive protein (hsCRP)), diet (standard American diet, ketogenic, carnivore, vegetarian, vegan, kosher, halal, etc.), supplements and naturopathic treatments, work hazard exposures (asbestos, dust), treatments performed (ventilator), other tests performed (CT scan, IR scan, etc.), personal information (lung volume, CO2/O2 exchange volume, sleep pattern, weight, BMI, blood pressure, etc.), and positional/location tracking (GPS, Bluetooth, including PEPP-PT, the Pan-European Privacy-Preserving Proximity Tracing).

At the conclusion of the method 100, certain quantitative output will be generated. Governmental or healthcare professionals, corporations, or other individuals may then use the quantitative output to undertake a risk assessment.

In certain embodiments, the method 100 may output certain risk data, such as a minimum risk value regarding the percent of susceptibility that individual has to develop or spread an illness, such as COVID-19. The minimum risk value may then be reviewed and analyzed to determine whether the individual is outside of a risk threshold such that the individual may be allowed to engage in certain activities, such as travel or in-office work functions.

In certain embodiments, the collected data may include whether an individual has been treated with a certain pharmaceutical, such as malaria treatment or ACE inhibitors. Based on that information, at the conclusion of the method 100, certain quantitative data will be output to predict any percent increase or decrease in the individual's susceptibility to an illness based on whether they have or have not been treated with the pharmaceutical.

In certain embodiments, the method 100 may output quantitative data regarding the likelihood that an individual will develop certain symptoms of a medical condition, and this information may be used to predict whether the individual will need to be treated using particular treatment resources. For example, in predicting susceptibility to COVID-19, the method may output qualitative data regarding a likelihood that the individual will develop lung failure and require ventilator treatment. Such data is useful for government, healthcare organizations, or other corporations to predict resource usage (e.g., how many ventilators may be needed to treat a given population) in response to a pathogen and illnesses caused therefrom.

After identification is performed according to methods disclosed herein, such as the method 100 illustrated in FIG. 1, the patient may be treated using one or more treatments. These treatments may be identified, for example using additional machine learning models trained to identify treatments with a high likelihood of success and with low risk of serious side effects.

It is contemplated that the method 100 may be used to analyze large data sets, such as data from a hospital, to determine susceptibility of a population or subset thereof. It is also contemplated that the method 100 may be used as a self-assessment tool for an individual to input personal data to determine their individual susceptibility to an illness.

Embodiments of the present disclosure advantageously replace qualitative conjecture with quantitative evidence, utilizing data science to model the complex relationships as it pertains to illnesses. Embodiments of the present disclosure may be used by individuals to identify their own risks or by doctors, corporations or governments to service or identify exposure for outbreaks that may affect any being.

Example Prediction of Susceptibility of Living Organisms to Medical Conditions Based on Machine Learning Models Living organisms may have different levels of susceptibility to medical conditions, such as illnesses caused by pathogens (e.g., severe respiratory distress syndrome caused by the SARS-COV-2 virus), cancer, auto-immune disorders, or other causes, based on various factors. For example, humans with a certain blood type may be more susceptible to a medical condition than humans with other blood types. In another example, humans who are overweight and/or do not perform a large amount of physical activity may be more susceptible to medical conditions, such as cardiovascular diseases or diabetes, than humans who are not clinically overweight and/or are physically active. In still further examples, other attributes, such as exposure to different chemical compounds, or the like, may affect a patient's susceptibility to various medical conditions.

To improve the health of a living organism and prevent or mitigate the effects of these various medical conditions, various actions may be recommended to reduce the organism's risk. These actions may include prescribing various medications (which may be more or less effective for different types of patients based on the unique attributes associated with these patients), recommending foods or activities to seek or avoid, recommending minimization of exposure to certain chemical agents, and the like. For human patients, these actions may generally be recommended by a physician based on generically applicable principles, which may cause recommendations to be made that may not be optimal for any given patient. Further, these recommendations may be used by various entities to determine actions to implement based on risks, even though these recommendations may be more relevant for organisms having higher susceptibility to a medical condition than organisms with lower susceptibility to the medical condition Aspects of the present disclosure provide machine learning techniques that allow for susceptibility of a living organism to a medical condition to be predicted, which in turn may be used to recommend treatments for the living organism based on the predicted susceptibility to the medical condition. By using machine learning models to predict susceptibility of a living organism to a medical condition based on various patient attributes, aspects of the present disclosure may allow for more accurate targeting of medical interventions, in some cases prior to the living organism being afflicted by a medical condition, based on the susceptibility of that living organism to the medical condition. Intervening actions may, in some aspects, be identified and implemented long before the living organism is afflicted by the medical condition, which may thus provide for improvements to the health of those living organisms.

Figure 4:
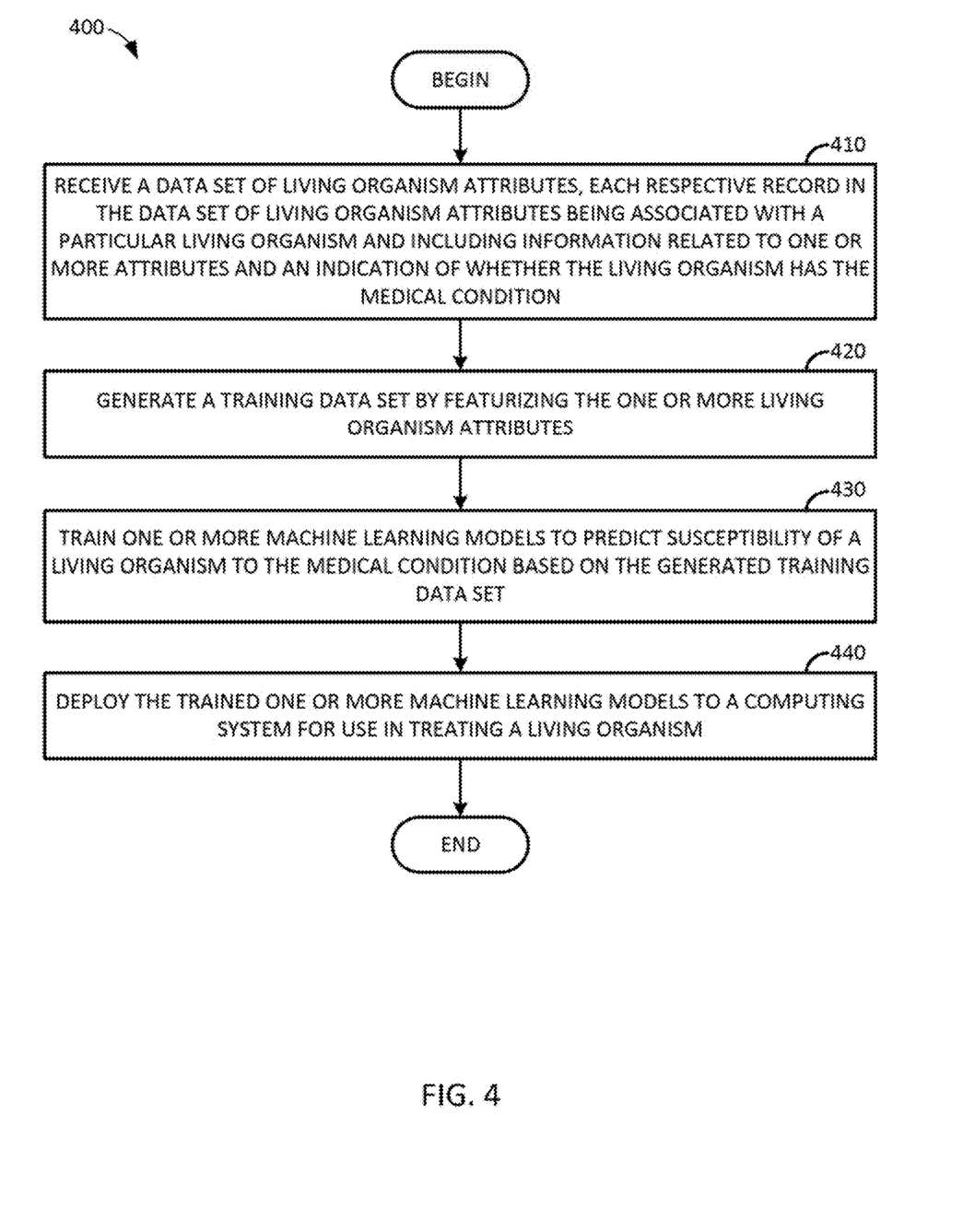
FIG. 4 illustrates example operations that may be performed by a computing system to train one or more machine learning models to predict patient susceptibility to a medical condition, according to embodiments of the present disclosure.

FIG. 4 illustrates example operations for training a machine learning model to predict susceptibility of a living organism to a medical condition, according to certain aspects described herein.

As illustrated, operations 400 may begin at block 410, where a computing system receives a data set of living organism attributes. The data set of living organism attributes may include a plurality of records, and each record in the data set may be associated with a particular living organism and may include information related to one or more attributes and an indication of whether the living organism has a medical condition.

In some aspects, the data set of living organism attributes may be received from a plurality of data sources and may be aggregated into a unified data set prior to training one or more machine learning models. The plurality of data sources may include, for example, a secure medical records repository (e.g., a repository of patient medical records subject to the privacy and security requirements of the Health Insurance Portability and Accountability Act or other relevant data privacy regulations) and from one or more other external data sources, such as activity trackers, patient surveys, exposure counters, wearable medical devices, or the like. Generally, to aggregate the data into the unified data set, information from each of a plurality of sources can be mapped to one or more attributes in the unified data set into which information about a living organism is to be mapped, and the appropriate values may be filled into the attributes in the unified data set from the appropriate data source.

The attributes included in each record in the received data set may include a variety of medical, activity, environmental, and other information about or received from the living organism associated with the record. The medical information may include, for example, information such as blood type, blood pressure, known conditions that the living organism has, prior surgical history, prescription medications that the user is taking (including, but not limited to, the trade name or active ingredient(s) of the medication and dosage information), family medical history, habits, and the like. The activity information may include, for example, an average number of calories burned per day, an amount of time the patient spent exercising, and the like. Environmental information may include, for example, indications of whether the user has been exposed to or is regularly exposed to various chemicals or types of radiation, the amount of exposure, and/or other environmental information that may influence susceptibility of a living organism to a medical condition.

At block 420, the computing system generates a training data set by featurizing the one or more living organism attributes. To featurize the one or more living organism attributes, the raw data in each record in the received data set may be transformed into machine-readable or machine-usable data that can be used to train a machine learning model. Generally, raw data may be transformed into numerical data representing, for example, a binary choice (e.g., whether a living organism is associated with a given attribute or is not associated with the given attribute, such as whether a living organism has a given medical condition, is taking a given medication, or the like), one of a plurality of categories (e.g., where an attribute has a range of values, and different sub-ranges are probative of different levels of susceptibility to a medical condition, such as ranges of weight, ranges of exposure, etc.), or numerical data scaled based on a scaling factor.

The computing system can use one or more predefined rules to determine how to featurize each of the one or more living organism attributes. Each attribute to be included in a training data set may be associated with a rule indicating how the underlying raw data from the received data set is to be transformed into a feature usable in training a machine learning model to predict susceptibility to a medical condition. In some aspects, the rules may define how multiple related data items may be aggregated into a single value, and the single value may be featurized. In another example, multiple different values may map to a same featurized value. For example, if an attribute is whether a patient has been prescribed or is otherwise taking over-the-counter allergy medication (e.g., a binary feature), it may be recognized that there are many types of allergy medications that a patient can be taking. Thus, the rule may recognize that if the data set includes information indicating that the patient is taking one of the various types of allergy medications, regardless of the exact active ingredient or form of administration. In another example, the rules may define upper and lower bound values for classification of an attribute into one of a plurality of categories. For example, given patient weight and height as information included in a record in the received data set, an attribute may be defined as the patient's body mass index (BMI), and different values may be assigned to the attribute based on different BMI ranges (e.g., where a first value corresponds to underweight BMIs, a second value corresponds to normal BMIs, a third value corresponds to overweight BMIs, and a fourth value corresponds to obese BMIs).

In some aspects, some attributes may be determined based on raw data, and the one or more predefined rules may specify a scaling factor associated with the devices that recorded the raw data to use in scaling the data (e.g., prior to featurization). The scaling factor may be, for example, associated with an accuracy of a measurement device, which may be defined a priori according to manufacturer specifications or prior experience with the measurement device. For example, where a living organism attribute includes a size of an anatomical feature captured using one or more imaging devices (e.g., X-ray machines, magnetic resonance imagery machines, computed tomography (CT) machines, etc.), the raw size information may be adjusted based on an expected measurement error for the source imaging device. If, for example, an imaging device is known to be accurate to within n percent, the raw data may be scaled to a value of 100+n percent or 100−n percent, depending on the specific direction of error, developer choice, or the like. The scaled value may be preserved as the value associated with an attribute or may be further featurized into a binary feature or a feature with a fixed set of values, as discussed above.

In some aspects, the attributes included in the received data set may be reduced based on various filtering or selection techniques. It may be noticed, for example, that records include similar values for a particular attribute, regardless of whether the living organism has the medical condition. Because values for the particular attribute are similar for disparate outcomes across records in the data set, it may be determined that the attribute is not probative of whether the living organism is susceptible to the medical condition. Thus, the attribute may be removed from each of the records in the data set, which may reduce the amount of data processed while training the machine learning models. In another example, statistical tests can be used to determine whether an attribute is independent or dependent by using techniques such as chi-squared testing to determine whether observations deviate from an expected outcome for a particular analysis. In still further examples, various machine learning techniques can be used to assign an importance or significance value to each attribute. Attributes in the received data set having importance or significance values exceeding a threshold value may be retained in the received data set, while attributes having importance or significance values below the threshold value may be removed from the received data set.

In some aspects, the data set may not include a value for an attribute for a given living organism. To allow for each of the records in the data set to have a same number of attributes, the record for that given living organism may be modified with a value for the attribute indicating that the attribute does not apply to the living organism. For example, the value for the attribute may be a reserved value (e.g., a predefined magic number), a null value, or the like.

At block 430, the computing system trains one or more machine learning models to predict susceptibility of a living organism to the medical condition based on the generated training data set. The one or more machine learning models may be various types of machine learning models configured to generate various outputs. For example, the machine learning models may include one or more of probabilistic models, neural networks, clustering models, or other appropriate machine learning models. Generally, a probabilistic model may be configured to generate a probability distribution over a binary choice of options, where the probability value associated with having the medical condition is treated as a proxy for or otherwise indicative of susceptibility of a living organism to the medical condition. A clustering algorithm may be used to identify living organisms having similar attributes to a given living organism whose attributes are received as input. Information about the identified living organisms can then be used, as discussed in further detail below, to determine whether the patient is susceptible to the medical condition. For example, the ratio of living organisms in the group of identified patients having the medical condition to the total number of living organisms in the group of identified living organisms may be used as a proxy for or a value otherwise indicative of patient susceptibility to the medical condition.

At block 440, the computing system deploys the trained one or more machine learning models to one or more other computing systems for use in treating a living organism. As discussed in further detail below, these computing systems can use the trained machine learning models to determine whether the living organism is susceptible to the medical condition. Based on a determination of susceptibility of the living organism to the medical condition, the computing system can identify one or more treatments for the living organism to reduce the living organism's susceptibility to the medical condition.

Figure 5:
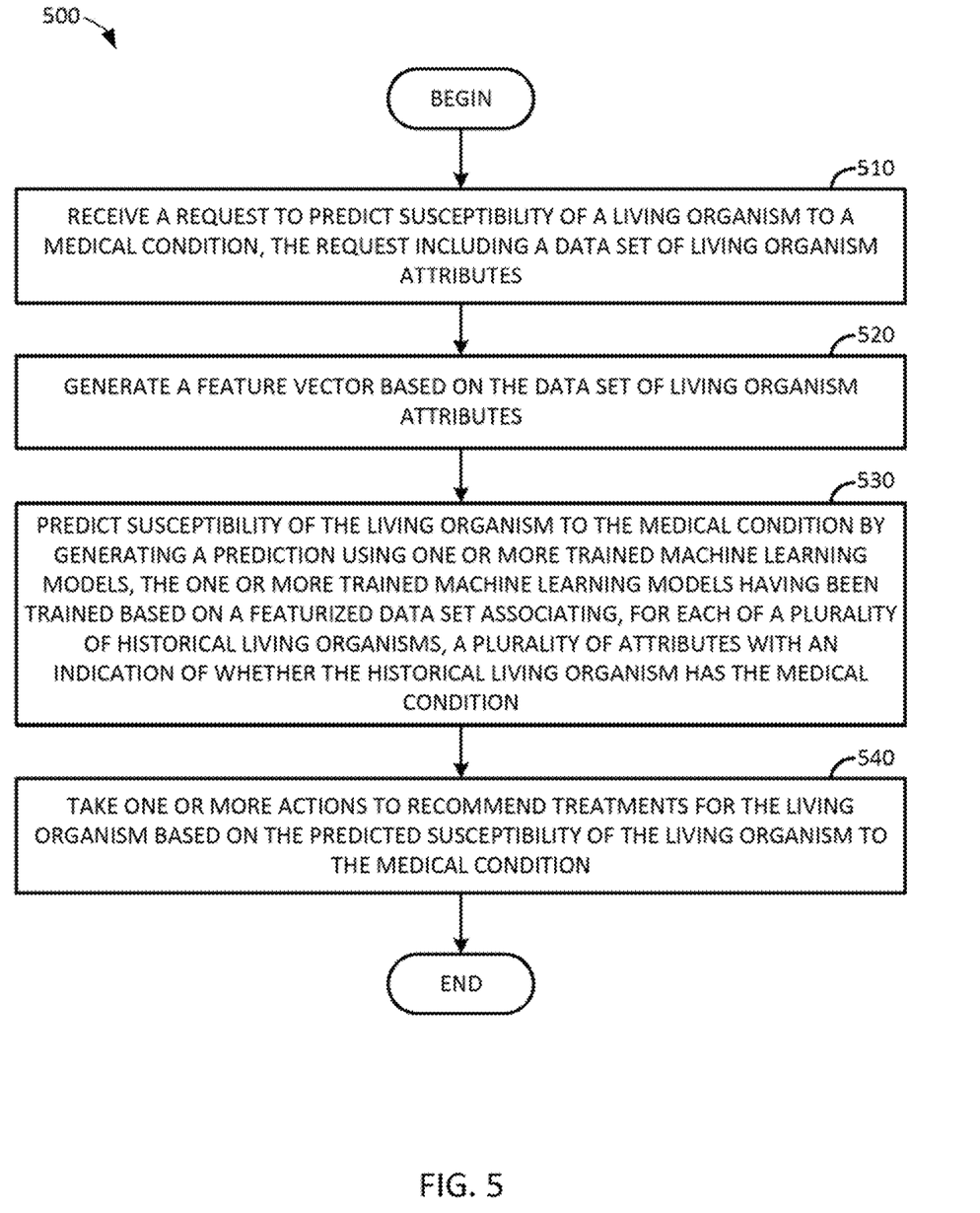
FIG. 5 illustrates example operations that may be performed by a computing system to predict patient susceptibility to a medical condition using one or more trained machine learning models, according to embodiments of the present disclosure.

FIG. 5 illustrates example operations 500 that may be performed by a computing system to predict susceptibility of a living organism to a medical condition based on one or more machine learning models.

As illustrated, operations 500 may begin at block 510, where the computing system receives a request to predict susceptibility of a living organism to the medical condition. The request generally includes a raw data set of living organism attributes. Like the records discussed above with respect to a data set used to train the one or more machine learning models, the raw data set of living organism attributes may include information from a secure medical records repository and from one or more other external data sources, such as activity trackers, patient surveys, exposure counters, wearable medical devices, or the like.

The attributes included in request may include a variety of medical, activity, environmental, and other information about or received from the living organism associated with the record. The medical information may include, for example, information such as blood type, blood pressure, known conditions that the living organism has, prior surgical history, prescription medications that the user is taking (including, but not limited to, the trade name or active ingredient(s) of the medication and dosage information), family medical history, habits, and the like. The activity information may include, for example, an average number of calories burned per day, an amount of time spent exercising, and the like. Environmental information may include, for example, indications of whether the living organism has been exposed to or is regularly exposed to various chemicals or types of radiation, the amount of exposure, and/or other environmental information that may influence patient susceptibility to a medical condition.

At block 520, the computing system generates a feature vector based on the data set of living organism attributes. As discussed, to generate the feature vector, the computing system can transform the raw data in the request into machine-readable or machine-usable data that can be used to train a machine learning model. Generally, raw data may be transformed into numerical data representing, for example, a binary choice (e.g., whether a patient is associated with a given attribute or is not associated with the given attribute, such as whether a living organism has a given medical condition, is taking a given medication, or the like), one of a plurality of categories (e.g., where an attribute has a range of values, and different sub-ranges are probative of different levels of susceptibility to a medical condition, such as ranges of weight, ranges of exposure, etc.), or numerical data scaled based on a scaling factor.

The computing system can use one or more predefined rules to determine how to featurize each of the one or more living organism attributes. Each attribute to be used in predicting susceptibility of the living organism to the medical condition may be associated with a rule indicating how the underlying raw data from the received data set is to be transformed into a feature usable by a machine learning model to predict susceptibility to a medical condition. In some aspects, the rules may define how multiple related data items may be aggregated into a single value, and the single value may be featurized. In another example, multiple different values may map to a same featurized value. In another example, the rules may define upper and lower bound values for classification of an attribute into one of a plurality of categories.

In some aspects, some attributes may be determined based on raw data, and the one or more predefined rules may specify a scaling factor associated with the devices that recorded the raw data to use in scaling the data (e.g., prior to featurization). The scaling factor may be, for example, associated with an accuracy of a measurement device, which may be defined a priori according to manufacturer specifications or prior experience with the measurement device. The scaled value may be preserved as the value associated with an attribute or may be further featurized into a binary feature or a feature with a fixed set of values, as discussed above.

In some aspects, the attributes included in the request may be reduced based on various filtering or selection techniques. The filtering or selection techniques may be defined based on the filtering or selection techniques used to filter data in a training data set used to train the one or more machine learning models. To reduce the information included in the feature vector down to a minimal set of information needed for the one or more machine learning models to predict susceptibility of the living organism to the medical condition, attributes that are known a priori to not be probative of whether someone is susceptible to the medical condition may be removed from the data set included in the request.

In some aspects, the data set may not include a value for an attribute. To allow for the feature vector to have a same number of attributes as the records in the training data set used to train the one or more machine learning models, the feature vector may be modified with a value for the attribute indicating that the attribute does not apply to the living organism. For example, the value for the attribute may be a reserved value (e.g., a predefined magic number), a null value, or the like.

At block 530, the computing system predicts susceptibility of the living organism to the medical condition by generating a prediction using one or more trained machine learning models. As discussed above, the machine learning models may have been previously trained based on a featurized data set associating, for each historical living organism of a plurality of historical living organisms, a plurality of attributes in patient medical history for the historical living organism with an indication of whether the historical living organism has the medical condition.

In some aspects, the one or more machine learning models may include probabilistic models that are trained to output, for a given input, a probability distribution over a universe of possible outcomes. In some aspects, the probability distribution may be generated over a binary selection of having the medical condition or not having the medical condition, with the probability value associated with having the medical condition serving as a proxy for susceptibility of the living organism to the medical condition. In some aspects, multiple probabilistic models can be used to predict susceptibility of the living organism to the medical condition, and each model of the multiple probabilistic models may be associated with a weighting value. A score serving as a proxy for susceptibility of the living organism to the medical condition may be calculated as a weighted average of the probability scores output by each of the multiple probabilistic models.

In some aspects, the one or more machine learning models may also or alternatively include one or more clustering models that are trained to identify a set of matching historical living organisms having similar data sets of attributes. To predict susceptibility of the living organism to the medical condition, a score can be generated based on the patients in the set of matching historical living organisms who are identified as having the medical condition. For example, a score may be generated based on a ratio of a number of historical living organisms in the set of matching historical living organisms who have the medical condition to the total number of historical living organisms in the set of matching historical patients.

In some aspects, a probabilistic model and a clustering model (as well as other machine learning models) may be used in conjunction with each other to predict susceptibility of a living organism to the medical condition. In one example, a probabilistic model may be associated with a first weighting value, and the clustering model may be associated with a second weighting value. The probability score—representing susceptibility of the living organism to the medical condition—may be calculated as sum of the score generated by the probabilistic model, weighted by the first weighting value, and the score generated by the clustering model, weighted by the second weighting value.

At block 540, the computing system takes one or more actions to recommend treatments for the living organism based on the predicted susceptibility of the living organism to the medical condition. To recommend treatments for the living organism, the system can, in some aspects, modify one or more values in the feature vector and predict susceptibility of the living organism to the medical condition using the modified feature vector. As various combinations of attribute modifications are processed through the machine learning model(s) (using the techniques discussed above), the computing system can identify which modifications lead to decreases in susceptibility to the medical condition and can output information about those modifications to a user for use in identifying one or more treatments to recommend for the living organism. In some aspects, the modifications may be identified in order of highest to lowest impact to predicted susceptibility to the medical condition, which may allow a doctor to identify and implement treatments that are most likely to reduce susceptibility to the medical condition.

Figure 6:
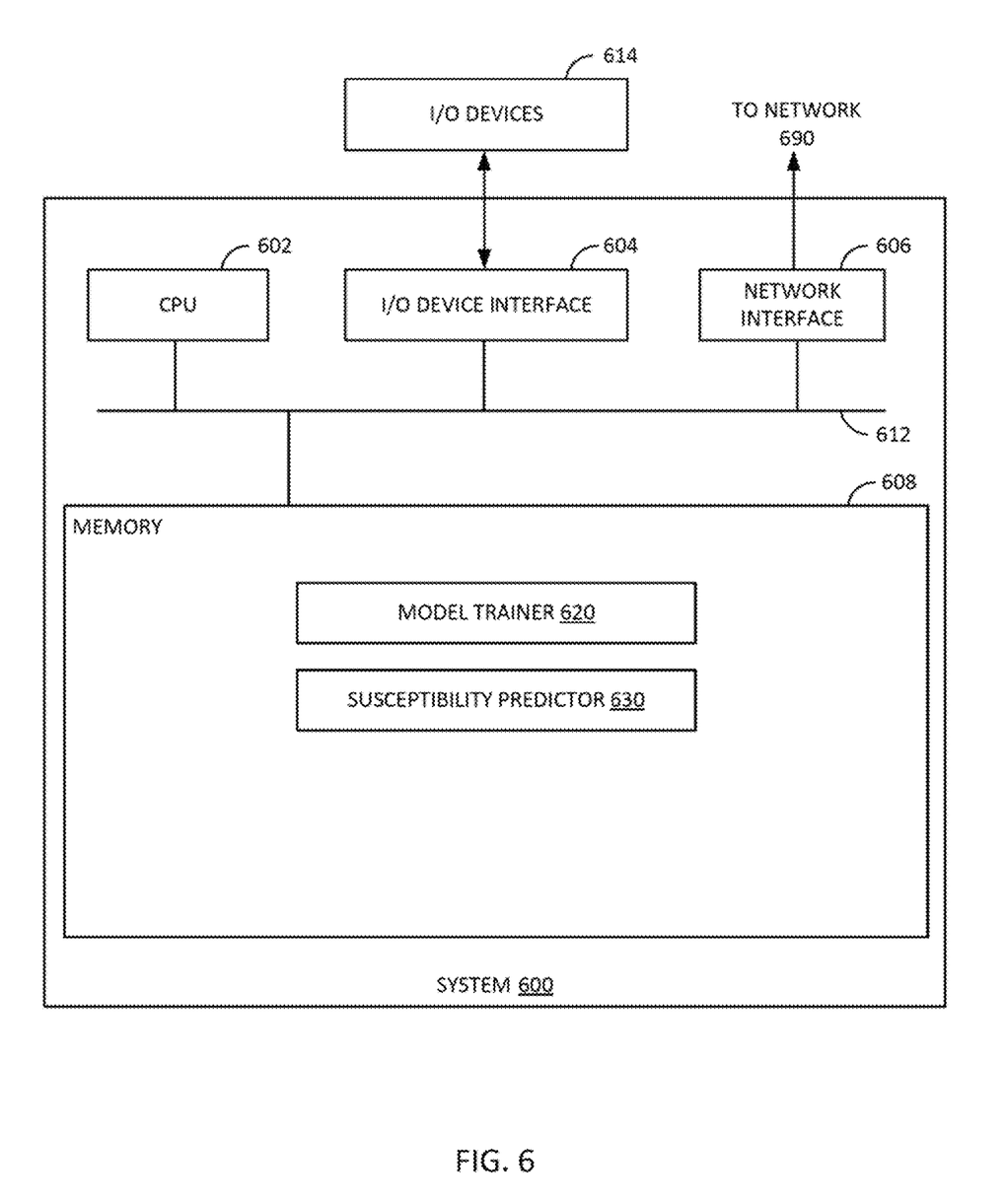
FIG. 6 illustrates an example system in which embodiments of the present disclosure may be implemented.

Example Systems for Predicting Susceptibility of a Living Organism to a Medical Condition Using Machine Learning Models FIG. 6 illustrates an example system 600 that can train and use machine learning models to predict susceptibility of a living organism to a medical condition, according to certain embodiments described herein.

As shown, system 600 includes a central processing unit (CPU) 602, one or more I/O device interfaces 604 that may allow for the connection of various I/O devices 614 (e.g., keyboards, displays, mouse devices, pen input, etc.) to the system 600, network interface 606 through which system 600 is connected to network 660 (which may be a local network, an intranet, the internet, or any other group of computing devices communicatively connected to each other), a memory 608, storage 610, and an interconnect 612.

CPU 602 may retrieve and execute programming instructions stored in the memory 608. Similarly, the CPU 602 may retrieve and store application data residing in the memory 608. The interconnect 612 transmits programming instructions and application data, among the CPU 602, I/O device interface 604, network interface 604, memory 608, and storage 610.

CPU 602 is included to be representative of a single CPU, multiple CPUs, a single CPU having multiple processing cores, and the like.

Memory 608 is representative of a volatile memory, such as a random access memory, or a nonvolatile memory, such as nonvolatile random access memory, phase change random access memory, or the like. As shown, memory 608 includes a model trainer 620 and a susceptibility predictor 630.

Model trainer 620 may be configured to perform the operations discussed herein (e.g., with respect to operations 400 illustrated in FIG. 4 and/or other operations) to train and deploy one or more machine learning models for predicting susceptibility of a living organism (e.g., a human patient) to a medical condition. As discussed, model trainer 620 can receive data from a plurality of data sources (including, but not limited to, a secure medical records data source, a physical activity records data source, a medicine usage data source, and/or other data sources in which attributes that may be predictive, alone or in isolation, of susceptibility to a medical condition may be stored) and generate a training data set by featurizing the one or more attributes. Model trainer 620 may be configured to train one or more machine learning models based on the generated training data set. As discussed, the one or more machine learning models may include probabilistic models, clustering-based models, and/or other machine learning models that may be used to predict susceptibility of a living organism to a medical condition given some input of a plurality of living organism attributes. Model trainer 620 may then deploy the trained one or more machine learning models for use (e.g., to patient susceptibility predictor 630 and/or one or more external computing systems accessible via network 660).

Susceptibility predictor 630 may be configured to perform the operations discussed herein (e.g., with respect to operations 500 illustrated in FIG. 5 and/or other operations) to predict susceptibility of a living organism to a medical condition and recommend actions to mitigate susceptibility of the living organism to the medical condition. As discussed, susceptibility predictor 630 may use the one or more machine learning models trained by model trainer 620 to generate predictions of susceptibility of the living organism to the medical condition. To do so, susceptibility predictor 630 can receive a request including a data set of living organism attributes and generate a feature vector based on the data set of living organism attributes. The feature vector may be provided as input into one or more machine learning models to generate a score that predicts susceptibility of the living organism to a medical condition. Based on the generated score, susceptibility predictor 630 can take one or more actions to recommend treatments for the living organism based on the predicted susceptibility. For example, as discussed above, susceptibility predictor 630 can recommend actions that may lower the living organism's susceptibility to the medical condition (e.g., based on a predefined set of actions or solving an optimization problem using the trained machine learning model to identify interventions or actions that are most likely to reduce patient susceptibility to the medical condition).

ADDITIONAL CONSIDERATIONS

The preceding description is provided to enable any person skilled in the art to practice the various embodiments described herein. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. Also, features described with respect to some examples may be combined in some other examples. For example, an apparatus may be implemented or a method may be practiced using any number of the embodiments set forth herein. In addition, the scope of the disclosure is intended to cover such an apparatus or method that is practiced using other structure, functionality, or structure and functionality in addition to, or other than, the various embodiments of the disclosure set forth herein. It should be understood that any aspect of the disclosure disclosed herein may be embodied by one or more elements of a claim.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

The various illustrative logical blocks, modules and circuits described in connection with the present disclosure may be implemented or performed with a general purpose processor, a digital signal processor (DSP), an application specific integrated circuit (ASIC), a field programmable gate array (FPGA) or other programmable logic device (PLD), discrete gate or transistor logic, discrete hardware components, or any combination thereof designed to perform the functions described herein. A general-purpose processor may be a microprocessor, but in the alternative, the processor may be any commercially available processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

A processing system may be implemented with a bus architecture. The bus may include any number of interconnecting buses and bridges depending on the specific application of the processing system and the overall design constraints. The bus may link together various circuits including a processor, machine-readable media, and input/output devices, among others. A user interface (e.g., keypad, display, mouse, joystick, etc.) may also be connected to the bus. The bus may also link various other circuits such as timing sources, peripherals, voltage regulators, power management circuits, and the like, which are well known in the art, and therefore, will not be described any further. The processor may be implemented with one or more general-purpose and/or special-purpose processors. Examples include microprocessors, microcontrollers, DSP processors, and other circuitry that can execute software. Those skilled in the art will recognize how best to implement the described functionality for the processing system depending on the particular application and the overall design constraints imposed on the overall system.

If implemented in software, the functions may be stored or transmitted over as one or more instructions or code on a computer-readable medium. Software shall be construed broadly to mean instructions, data, or any combination thereof, whether referred to as software, firmware, middleware, microcode, hardware description language, or otherwise. Computer-readable media include both computer storage media and communication media, such as any medium that facilitates transfer of a computer program from one place to another. The processor may be responsible for managing the bus and general processing, including the execution of software modules stored on the computer-readable storage media. A computer-readable storage medium may be coupled to a processor such that the processor can read information from, and write information to, the storage medium. In the alternative, the storage medium may be integral to the processor. By way of example, the computer-readable media may include a transmission line, a carrier wave modulated by data, and/or a computer readable storage medium with instructions stored thereon separate from the wireless node, all of which may be accessed by the processor through the bus interface. Alternatively, or in addition, the computer-readable media, or any portion thereof, may be integrated into the processor, such as the case may be with cache and/or general register files. Examples of machine-readable storage media may include, by way of example, RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The machine-readable media may be embodied in a computer-program product.

A software module may comprise a single instruction, or many instructions, and may be distributed over several different code segments, among different programs, and across multiple storage media. The computer-readable media may comprise a number of software modules. The software modules include instructions that, when executed by an apparatus such as a processor, cause the processing system to perform various functions. The software modules may include a transmission module and a receiving module. Each software module may reside in a single storage device or be distributed across multiple storage devices. By way of example, a software module may be loaded into RAM from a hard drive when a triggering event occurs. During execution of the software module, the processor may load some of the instructions into cache to increase access speed. One or more cache lines may then be loaded into a general register file for execution by the processor. When referring to the functionality of a software module, it will be understood that such functionality is implemented by the processor when executing instructions from that software module.

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112(f) unless the element is expressly recited using the phrase "means for" or, in the case of a method claim, the element is recited using the phrase "step for." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. A method for predicting susceptibility of a living organism to a medical condition based on one or more machine learning models, comprising:
   receiving a request to predict susceptibility of the living organism to the medical condition, the request including a data set of living organism attributes;
   generating a feature vector based on the data set of living organism attributes;
   predicting susceptibility of the living organism to the medical condition by generating a prediction using one or more trained machine learning models, the one or more trained machine learning models having been trained based on a featurized data set associating, for each historical living organism of a plurality of historical living organisms, a plurality of data points in medical history for the historical living organism with an indication of whether the historical living organism has the medical condition; and
   taking one or more actions to recommend treatments for the living organism based on the predicted susceptibility of the living organism to the medical condition;
   wherein the one or more trained machine learning models comprise one or more probabilistic models trained to generate a probability distribution corresponding to a likelihood of the living organism having the medical condition and a likelihood of the living organism not having the medical condition, and
   wherein predicting susceptibility of the living organism to the medical condition comprises generating a probability score as a weighted average of probabilities of having the medical condition generated by each of the one or more trained machine learning models, each model of the one or more trained learning model being associated with a weighting value to assign to a likelihood of the living organism having the medical condition.

2. The method of claim 1, wherein:
   the one or more trained machine learning models comprise a probabilistic model configured to output a probability that the living organism is susceptible to the medical condition and a clustering model configured to output a ratio of historical living organisms having the medical condition in a set of matching historical living organisms to a total number of historical living organisms in the set of matching historical living organisms, and
   the predicted susceptibility of the living organism comprises a weighted average of the probability that the living organism is susceptible to the medical condition and the ratio of historical living organisms having the medical condition to the total number of historical living organisms in the set of matching historical living organisms.

3. The method of claim 1, wherein generating the feature vector comprises: for each attribute in the data set, assigning one of a plurality of numerical values for the attribute based on a value of the attribute in the data set, each value indicating a classification of the respective attribute into one of a plurality of categories.

4. The method of claim 1, wherein generating the feature vector comprises:
   scaling a value of an attribute in the data set based on a scaling factor associated with an accuracy of a source from which the value was obtained; and
   featurizing the scaled value of the item.

5. The method of claim 1, wherein generating the feature vector comprises: replacing null values for features in the data set with an indication that the features do not apply to the living organism.

6. The method of claim 1, wherein the medical condition comprises respiratory complications caused by SARS-COV2.

7. A method for predicting susceptibility of a living organism to a medical condition based on one or more machine learning models, comprising:
   receiving a request to predict susceptibility of the living organism to the medical condition, the request including a data set of living organism attributes;
   generating a feature vector based on the data set of living organism attributes;
   predicting susceptibility of the living organism to the medical condition by generating a prediction using one or more trained machine learning models, the one or more trained machine learning models having been trained based on a featurized data set associating, for each historical living organism of a plurality of historical living organisms, a plurality of data points in medical history for the historical living organism with an indication of whether the historical living organism has the medical condition; and
   taking one or more actions to recommend treatments for the living organism based on the predicted susceptibility of the living organism to the medical condition;
   wherein the one or more trained machine learning models comprise one or more clustering models trained to identify a set of matching historical living organisms of the plurality of historical living organisms having similar data sets of patient attributes to the living organism, and wherein predicting susceptibility of the living organism to the medical condition comprises calculating a ratio of a number of historical living organism in the set of matching historical patients having the medical condition to a total number of historical living organisms in the set of matching historical patients.

8. The method of claim 7, wherein the medical condition comprises respiratory complications caused by SARS-COV2.

9. A method for predicting susceptibility of a living organism to a medical condition based on one or more machine learning models, comprising:

receiving a request to predict susceptibility of the living organism to the medical condition, the request including a data set of living organism attributes;

generating a feature vector based on the data set of living organism attributes;

predicting susceptibility of the living organism to the medical condition by generating a prediction using one or more trained machine learning models, the one or more trained machine learning models having been trained based on a featurized data set associating, for each historical living organism of a plurality of historical living organisms, a plurality of data points in medical history for the historical living organism with an indication of whether the historical living organism has the medical condition; and taking one or more actions to recommend treatments for the living organism based on the predicted susceptibility of the living organism to the medical condition;

wherein the one or more trained machine learning models comprise a probabilistic model configured to output a probability that the living organism is susceptible to the medical condition and a clustering model configured to output a ratio of historical living organisms having the medical condition in a set of matching historical living organisms to a total number of historical living organisms in the set of matching historical living organisms, and wherein the predicted susceptibility of the living organism comprises a weighted average of the probability that the living organism is susceptible to the medical condition and the ratio of historical living organisms having the medical condition to the total number of historical living organisms in the set of matching historical living organisms.

10. The method of claim 9, wherein the medical condition comprises respiratory complications caused by SARS-COV2.

* * * * *